United States Patent
Khurai

(10) Patent No.: US 10,751,166 B2
(45) Date of Patent: Aug. 25, 2020

(54) METHOD FOR PERFORMING OPHTHALMOSURGICAL OPERATIONS USING AN AUTOGRAFT

(71) Applicant: Aslan Ramazanovich Khurai, Moscow Oblast (RU)

(72) Inventor: Aslan Ramazanovich Khurai, Moscow Oblast (RU)

( * ) Notice: Subject to any disclaimer, the term of this patent is extended or adjusted under 35 U.S.C. 154(b) by 137 days.

(21) Appl. No.: 15/756,787

(22) PCT Filed: Aug. 30, 2016

(86) PCT No.: PCT/RU2016/000584
§ 371 (c)(1),
(2) Date: Mar. 1, 2018

(87) PCT Pub. No.: WO2017/039488
PCT Pub. Date: Mar. 9, 2017

(65) Prior Publication Data
US 2018/0289468 A1 Oct. 11, 2018

(30) Foreign Application Priority Data
Sep. 2, 2015 (RU) ................................ 2015137410

(51) Int. Cl.
| | | |
|---|---|---|
| *A61F 2/14* | (2006.01) | |
| *A61F 9/00* | (2006.01) | |
| *A61F 9/007* | (2006.01) | |
| *A61L 27/36* | (2006.01) | |
| *A61B 17/00* | (2006.01) | |

(52) U.S. Cl.
CPC ............ *A61F 2/142* (2013.01); *A61F 9/007* (2013.01); *A61F 9/0017* (2013.01); *A61L 27/362* (2013.01); *A61L 27/3641* (2013.01); *A61B 2017/00969* (2013.01); *A61F 2230/0008* (2013.01); *A61F 2230/0013* (2013.01); *A61F 2230/0019* (2013.01); *A61F 2230/0065* (2013.01); *A61F 2230/0069* (2013.01); *A61L 2430/16* (2013.01)

(58) Field of Classification Search
CPC ................................ A61F 2/142; A61F 9/0017
See application file for complete search history.

(56) References Cited

U.S. PATENT DOCUMENTS

| | | | | |
|---|---|---|---|---|
| 4,057,055 A | * | 11/1977 | Clark | ........................ A61F 5/11 602/31 |
| 5,712,252 A | * | 1/1998 | Smith | ................ A61K 38/1709 424/423 |
| 5,824,086 A | * | 10/1998 | Silvestrini | ............... A61F 2/147 623/5.11 |
| 6,544,286 B1 | * | 4/2003 | Perez | ...................... A61F 2/142 623/4.1 |
| 8,394,140 B2 | | 3/2013 | Chapoy et al. | |
| 2004/0073303 A1 | * | 4/2004 | Schanzlin | ............... A61F 2/147 623/5.16 |
| 2011/0117169 A1 | * | 5/2011 | Sanford | ............... A61K 9/0024 424/423 |
| 2014/0107778 A1 | | 4/2014 | Delhom Munoz et al. | |

FOREIGN PATENT DOCUMENTS

| | | |
|---|---|---|
| RU | 1771730 | 10/1992 |
| RU | 2367379 C1 | 9/2009 |
| RU | 2375025 C1 | 12/2009 |
| RU | 2008136051 | 4/2010 |
| RU | 2436553 | 12/2011 |
| RU | 2491962 C1 | 9/2013 |
| RU | 2519357 C2 | 6/2014 |
| RU | 2525673 C2 | 8/2014 |
| SU | 388746 | 7/1973 |
| SU | 1209211 | 2/1986 |
| WO | WO2014036622 A1 | 3/2014 |

OTHER PUBLICATIONS http://mediphacos.com/en/products/corneal/keraring-anel-intraestromal/.
Dasker, Albert, J. Cataract Refract Surg, 2008, 34, pp. 194-198.
Colin, J. et al., Current surgical options for keratoconus, J. Cataract Refract Surg, 2003, 29(2): pp. 379-386 (the abstract) [on-line] Found from PubMed, PMID: 12648653.
Puchkovsky H. et al., "Intragenic Strengthening Keratoplasty" (https://www.glazmed.ru/lib/burn/burn-0100.shtml).

* cited by examiner

*Primary Examiner* — Leslie Lopez
(74) *Attorney, Agent, or Firm* — McCarter & English, LLP; Vadim E. Cherkasov

(57) ABSTRACT

The claimed method for performing ophthalmosurgical operations includes forming a recipient bed and implanting an autograft consisting of a portion of the patient's own nail plate, which is shaped to fit the recipient bed, and which is sterilized and then kept in a dry environment prior to implantation. The autograft is similar in chemical composition and physical characteristics to the tissues of the eye, is not accompanied by an immune system rejection reaction, and adapts to the shape of the recipient bed as a result of natural swelling.

20 Claims, 1 Drawing Sheet

METHOD FOR PERFORMING OPHTHALMOSURGICAL OPERATIONS USING AN AUTOGRAFT

CROSS-REFERENCE TO RELATED APPLICATIONS

This application is a U.S. National Phase Application under 35 U.S.C. 371 of International Application No. PCT/RU2016/000584 filed Aug. 30, 2016, which was published on Mar. 9, 2017 under International Publication Number WO 2017/039488, and which claims the benefit of priority to Russian Patent Application No. 2015137410 filed Sep. 2, 2015. The entire contents of each of the two foregoing patent applications are incorporated herein by reference in their entireties.

TECHNICAL FIELD

The invention relates to medicine, specifically to ophthalmology, and may be used when performing a wide range of surgical operations.

PRIOR ART

It is known that transplants are used in a number of ophthalmosurgical operations for correcting myopia, hypermetropia, presbyopia and treatment of corneal ectasia, as one of the most serious complications of corneal refractive surgery, retinal detachment, scleroplasty in progressive myopia and other pathologies. Thus, intrastromal keratoplasty with implantation of corneal segments is used for treating patients with idiopathic and iatrogenic forms of ectasia: stable and progressive keratoconus, pellucid marginal corneal degeneration, keratectasia after LASIK, irregular astigmatism, i.e. the segment performs an orthopedic function.

Several modifications are described, both of the segments themselves (with respect to height, length, radius of curvature, shape of cross section, material), and of the technique for implanting them (with respect to depth, number of segments to be implanted (1 or 2), location of the corneal incision (on the strong or weak meridian)).

The use of various materials both of synthetic and of native origin in ophthalmic surgery is known. Thus, a graft for scleroplasty has a polymer base, on which a porous layer of the same polymer is applied (RU2491962 C1, ZAO NPK "Ekoflon", Sep. 10, 2013); intracorneal graft made of an inert plastic—polymethylmethacrylate (SU0388746, MNI-IGB, Zhivotovskii, Jul. 5, 1973; RU2375025 C1, FGU MNTK "Mikrokhirurgiya glaza" [Microsurgery of the eye], Dec. 10, 2009; RU2436553 C1, UfNII GB AN RB, Dec. 20, 2011), and other polymers with varying elastic modulus (U.S. Pat. No. 5,824,086, KeraVision, Inc., Oct. 20, 1998; U.S. Pat. No. 8,394,140, Chapoy, et al., Mar. 12, 2013); of variable section US2014107778 (A1)—INTRASTROMAL SEGMENT, IMEX CLINIC SL, Apr. 17, 2014; WO2014036622 (A1)—IMPLANTABLE DEVICE FOR MOULDING THE CURVATURE OF THE CORNEA, MEDIPHACOS LTDA, Mar. 13, 2014). A method has been described for performing an ophthalmosurgical operation, comprising making incisions for forming the recipient bed and implanting reinforcing elements of the graft in this bed (RU2525673 C2, UFA EYE DISEASE RESEARCH INSTITUTE, Aug. 20, 2014). Keraring artificial corneal segments from the company Mediphacos (http://www.mediphacos.com/en/produtos/cornea/implante-intracorneano-kerar-ing/) were used as the graft. A keratoprosthesis is described for surgical treatment of category IV-V leukomas, which contains an optical cylinder and a supporting plate, made from elastic porous titanium nickelide, which can be molded to the shape and curvature of the cornea (RU2367379 C1, Berezovskaya et al., Sep. 20, 2009).

However, one of the main drawbacks of artificial materials is that they are a foreign body for the cornea, they are encapsulated, and rejected, and they disturb the trophism of the cornea. There is still no consensus on the optimal artificial material for implantation in the layers (stroma) of the cornea.

An intracorneal allograft has been proposed in the form of a dehydrated donor cornea, having a rectangular shape in section (SU1209211, Sergienko et al., Feb. 7, 1986), and ribbonlike implants from a donor cornea (RU1771730, Shusterov et al., Oct. 30, 1992). Allografts have been described obtained from the sclera and dura mater or an autograft from auricle cartilage. Experimental studies have shown that such transplants take well and keep their structure and thickness (Puchkovskaya N. A. "Intracorneal reinforcing keratoplasty" http://www.glazmed.ru/lib/burn/burn-0100.shtml). Besides the autograft from auricle cartilage, a keratoprosthesis has been mentioned, the supporting plate of which consisted of an autograft of the alveolar process of the patient's tooth.

However, one of the main drawbacks of the aforementioned native materials for making transplants is as follows. With respect to their chemical composition and physical properties, they differ considerably from corneal tissue, and this in its turn may affect the optical and trophic functions of the cornea and limit the possibility of use and achievement of certain results (high refractive effect, variation of cornea geometry, maximum flattening, surface location of segments, thickness of segments, transport of nutrients, optical transparency, etc.).

DISCLOSURE OF THE INVENTION

The present invention aims to expand the arsenal of autograft materials that are similar in chemical composition and physical properties to the tissues of the eye, absence of a rejection reaction of the autograft by the immune system and at the same time are convenient for production, processing and transplantation.

The method to be patented for performing ophthalmosurgical operations comprises preparing a recipient bed and implanting at least one graft therein. As the material for making the graft, it is proposed to use a fragment of the patient's own nail plate, which is adapted to the shape of the recipient bed, and after sterilization prior to implantation, the autograft obtained is stored in a dry atmosphere.

The method may be characterized in that the ophthalmosurgical operations may include the following, although this is not an exhaustive list: refractive intrastromal keratoplasty, therapeutic intrastromal keratoplasty, scleroplasty, application of a keratoprosthesis, reconstruction of eye tissues after severe traumatic damage, in retinal detachment, stump formation after eyeball enucleation, in fractures of the bone walls of the orbit with entrapment of soft tissues, in operations for strabismus, as well as operations for glaucoma.

The method may also be characterized in that the autograft has the form of segments or rings or half-rings or lenses or plates, and in that the fragment of nail plate is obtained from grown nail, and in that the fragment of nail plate is obtained from the patient's nail under local anesthesia.

The method may in addition be characterized in that the autograft is made in the form of a half-ring with an arc of 150°-170°, height from 50 μm to 300 μm, inside and outside diameters of 4 mm and 5 mm respectively, and in that the graft is made in the form of a ring with inside diameter from 0.5 mm to 7 mm, outside diameter from 1.0 mm to 16 mm and height from 50 μm to 300 μm.

The method may also be characterized in that the autograft is made in the form of a positive lens with diameter from 1 mm to 7 mm with a central hole with a diameter from 0.1 mm to 5 mm, and in that the graft is made in the form of a plate with a length from 1 mm to 25 mm and width from 1 mm to 20 mm and thickness from 10 μm to 350 μm.

The method may also be characterized in that the autograft is shaped using a diamond cutter monitored with an operating microscope or using laser processing.

The technical result attainable on carrying out the method consists of the use of an autograft similar in its chemical composition and physical properties to the tissues of the eye, the possibility of adapting it to the shape of the recipient bed as a result of natural swelling, and absence of a reaction of rejection by the immune system.

This technical result has not been achieved previously in performing ophthalmosurgical operations and is unknown to the applicant, so that the method being patented is considered to meet the criterion of "inventive step".

The use of autografts from nail plates is known (Sitnikov V. P. et al. Use of autografts and implants in ossiculoplasty, Vestnik otorinolaringologii, No. 2, 2006 (http://www.mediasphera.ru/journals/oto/detail/45/397/). As stated in this article, the aim of the study was to " . . . perform a comparative analysis of the efficacy of ossiculoplasty when using two types of autografts—bone autografts and nail autografts, as well as titanium implants"; however, no significant dependence of the functional results of ossiculoplasty on the type and material of the prosthesis was found. In other words, for the purposes of ossiculoplasty, no importance attaches to "swelling" with change in dimensions of the prosthesis and transparency of the implanted material, as well as transport of nutrients.

The method being patented is based on properties of nail plates as a construction material that were in fact previously unknown for ophthalmic surgery. The nail plate autograft and the stroma of the cornea are of a construction similar in structure, physical properties and chemical composition. Since the nail plate is the body's own tissue, the body's immune system will not reject the implant, it will not be encapsulated, and it will not prevent the transport of nutrients to the tissues of the eye.

An important circumstance utilized in the present invention is that the nails react extremely sensitively to the external conditions of the environment, changing their volume and shape. In a cold and/or dry environment the nail plates contract, decreasing in volume. In a hot and/or moist environment the nails increase in volume. This property is also of direct importance in ophthalmosurgical practice, since, for example, on implantation in the corneal layer the graft must have smaller dimensions for convenience of implantation, and after implantation it must have larger dimensions, to obtain the maximum effect. The implant is in a moist, hot environment, it absorbs moisture and increases in volume, thereby filling the tunnel in the corneal stroma. This creates closer contact with the surrounding tissues of the cornea, which has a favorable effect on optical function, without creating aberration. Moreover, complete filling of the corneal tunnel prevents cavities in the corneal stroma, which may be filled with detritus and lipid deposits, causing an unpleasant picture in the form of white dot-like formations in the corneal stroma along the tunnel.

The starting material should be taken from a grown nail or directly from the nail plate under local anesthesia. Depending on the aims (implant thickness, dimensions), the material can be taken from different nail plates of the patient's hands or feet. The basic requirement for implantation is to take nail plate that is completely healthy, without fungal, bacterial or viral infection, as well as without structural defects.

After local anesthesia, a tourniquet is fitted at the base of the finger from which the nail plate will be removed. After this, the nail plate is secured with a special clamp and is separated from the nail bed. After removal of the nail plate, an aseptic dressing is placed on the nail bed and the tourniquet is removed. For nail plates, thickness of 0.30-0.45 mm on the fingers and 1 mm on the toes is regarded as normal. Depending on the purpose, the nail plate may be taken from the thumb or the big toe.

For making an autograft with precise geometric characteristics it is possible to use both mechanical and laser shaping means that provide a smooth, even surface. Chemical treatment may be used for increasing transparency. In subsequent sterilization it is possible to use both physical methods (autoclaving, lyophilization, gamma radiation and fast electrons), and available antibiotics, as well as chemical antiseptics (ethylene oxide, Katamin AB [benzalkonium chloride], chlorhexidine digluconate etc.). Lyophilization methods aid maximum preservation of the unique properties of the nail plate autograft with simultaneous dehydration and sterilization thereof.

It is convenient to use an aqueous solution of chlorhexidine digluconate, an antiseptic with primarily bactericidal action. The finished blank of the nail plate is kept in an aqueous solution of chlorhexidine digluconate and then the nail plate is transferred to sterile saline to remove the residues of chlorhexidine. Next, the nail plate autograft in dehydrated form is put in sterile packaging and stored until implantation. This method of treatment allows maximum preservation of low immunogenicity and of the physical and mechanical properties, which largely determine the results from use in clinical practice.

Thus, during preparation of the autograft there must be regular inspection of the properties and parameters both of the starting nail plate, and of the elements made from it, in accordance with the accepted standard in surgery and the requirements relating to implantable media and their histochemical and toxicological preparation.

VARIANT EMBODIMENTS OF THE INVENTION

Figure 1:
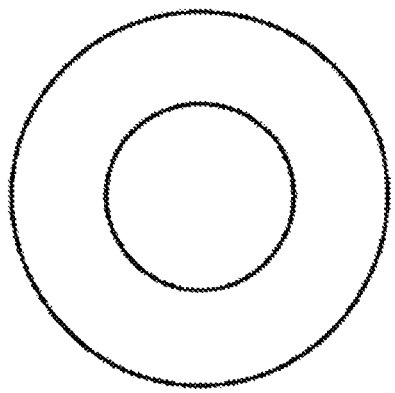
FIGS. 1-9 show some possible shapes of the autograft that can be made from the nail plate.

The shapes of the graft, which determine the efficacy of the treatment, are known per se by specialist ophthalmic surgeons and are not the subject matter of the present invention (FIGS. 1-9). The element may be modeled with respect to shape and dimensions using a diamond cutter monitored with an operating microscope, as noted in the aforementioned work by V. P. Sitnikov, or in some other known way, for example using laser cutting and milling on cutting machines, by means of which the nail plate material is given the necessary geometric parameters. The resultant article with the specified parameters undergoes chemical treatment if required, and then it is sterilized, and held in a dry atmosphere for drying, after which it is ready for implantation. The area of the patient's nail plates means it is possible to make corneal segments in the form of half-rings with an arc of about 160°, with a cross section of triangular shape and thickness of 150-350 μm, outside and inside diameters of approx. 5.6 mm and 4.4 mm respectively, i.e. with the same dimensions as Keraring segments made from polymethylmethacrylate.

The operation is performed by the usual surgical techniques developed for example for implantation of intrastromal disks and segments, moreover in the present invention a new technical result is achieved: adaptation of the element to the shape of the tunnel in the corneal stroma after implantation, as a result of natural swelling. Furthermore, the nail plate is similar in structure and composition to the corneal stroma, it is the body's own tissue, it will not be encapsulated and will not prevent nutrients being transported to the tissues of the eye.

Some examples of carrying out the invention are presented below.

Example 1

Intrastromal keratoplasty. Autografts are made individually depending on the parameters required for the patient, taking into account the degree and stage of the disease and the expected result. The operation is performed under local anesthesia. The patient's visual axis is determined by noting the reflected light with fixation of the eye on a light source. Then using a marker, a 5-7-millimeter zone is marked, simultaneously marking the strong meridian of the cornea and the diameter of the tunnel to be formed. A nonpenetrating incision with a length of 1-1.2 mm is made with a keratotomy knife. Intrastromal tunnels are formed using a special layer separator in the aforementioned zone, clockwise and counterclockwise to a predetermined depth. Segments from the patient's nail plates of the calculated thickness and length depending on the disease stage, type of ectasia, spherical equivalent, myopic and cylindrical component of refraction, are implanted. In the case of asymmetric ectasia, the thicker segment was placed in the lower hemisphere, and the thinner segment in the upper hemisphere. The patient is prescribed instillations of antibiotics and anti-inflammatory preparations.

Example 2

Intrastromal keratoplasty using an autograft in the form of a half-ring. Intrastromal tunnels were formed using a FEMTO LDV laser (ZIEMER, Switzerland) with wavelength of 1040-1060 nm, pulse repetition frequency of 1 MHz, pulse duration of 250 femtoseconds and pulse energy of 100 nJ. The operation was performed using an LCS (Lamellar Corneal Surgery) tip for ICR (intracorneal rings) of the FEMTO LDV module. The following parameters are entered in the program of the computer controlling the laser: model, arc length, thickness of the intrastromal segment and axis of the strong meridian.

Figure 2:
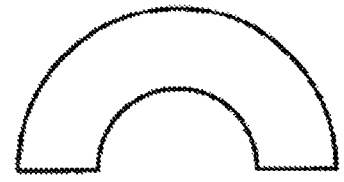
Figure 3:
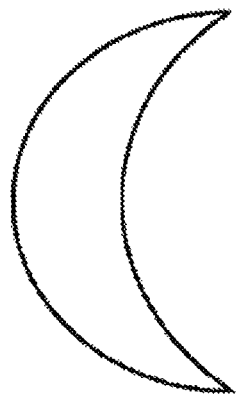
Figure 4:
Figure 5:
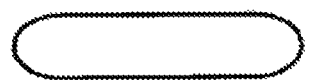
Figure 6:
Figure 7:
Figure 8:
Figure 9:
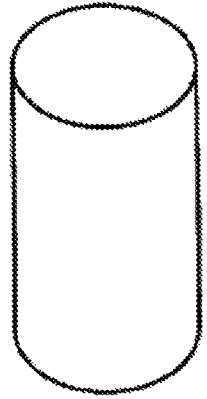

After applying local anesthesia, the patient's eyelids are fixed using a blepharostat, the LCS tip is fitted, and the patient fixes his gaze on the red fixation dot. Under the control of the computer program, the laser beam forms nonpenetrating tunnels. Then with a diamond knife, a 1-mm radial nonpenetrating incision is made on the principal meridian. The segments are introduced into the tunnel using forceps and a hook; they must be located symmetrically, away from the edge of the incision. We used corneal segments made from the patient's own nail plates, having the shape of a half-ring with an arc of 160°, and height of 100-250 μm, inside diameter of 4.4 mm, and outside diameter of 5.6 mm (FIG. 2). Instillations of anti-inflammatories, antibacterials and restorative preparations were made postoperatively.

Example 3

Intrastromal keratoplasty using a ring-shaped transplant. An intrastromal whole ring is made from nail plate individually, taking into account the degree of myopia to be corrected and the expected calculated result. The operation is performed under local anesthesia. An intrastromal pocket was formed using a PocketMaker microkeratome. The depth of formation of the intrastromal pocket is determined individually, depending on the degree of myopia.

After applying local anesthesia, the patient's eyelids are fixed using a blepharostat, the PocketMaker microkeratome is set up, and the patient fixes his gaze. Under the surgeon's control, the PocketMaker microkeratome forms a corneal pocket of the required depth and width, taking into account the myopia to be corrected and/or myopic astigmatism. The ring is implanted in the pocket formed, using forceps. Once fitted, the ring is centered relative to the optical axis of the eye using a push-and-pull hook. The operation ends with introduction of solution of antibiotic under the conjunctiva and fitting of a therapeutic lens on the cornea. We used autografts from the patient's own nail plates, having the shape of a ring, with height from 50 to 300 μm, inside diameter from 1 mm to 7 mm, and outside diameter from 1.5 mm to 10 mm (FIG. 1). Instillations of anti-inflammatories, antibacterials and restorative preparations were made postoperatively.

Example 4

Implantation of an intrastromal lens. Intrastromal lenses are made taking into account the degree of hypermetropia and/or presbyopia to be corrected and the expected calculated result. The operation is performed under local anesthesia. An intrastromal pocket was formed using a FEMTO LDV laser by the technology described in example 2.

After applying local anesthesia, the patient's eyelids are fixed using a blepharostat, the tip of the FEMTO LDV laser is fitted, and the patient fixes his gaze on the red fixation dot. Under the control of the computer program, the laser beam forms an intracorneal pocket. Then a radial nonpenetrating incision is made with a diamond knife. A segment in the form of a positive lens is introduced into the tunnel using forceps and a hook through the incision. The lens must be located centrally, away from the edge of the incision. Instillations of anti-inflammatories, antibacterials and restorative preparations were made postoperatively. We used corneal lenses made from the patient's nail plates, having the shape of a positive lens with a diameter from 1 mm to 5 mm and with a central hole from 0.1 mm to 3 mm. After implantation in the cornea, the intracorneal lens acts like a camera diaphragm, adjusting the depth of field, creating the possibility of near vision and distance vision. The principle of the action of this insert is that it blocks some light rays from nearby objects, which in presbyopia are not focused on the retina. This principle is the principle of the pinhole diaphragm, as used in photography, it provides depth of focus, and the result is clear vision at any distances.

Example 5

Applying a keratoprosthesis for treating severe opacification of the cornea of the eye. Through-application of a keratoprosthesis is carried out in a single step. After corneal trepanation, the keratoprosthesis is fitted along the visual axis of the eye until the supporting plate comes into contact with a pocket formed beforehand in the middle layers of the corneal stroma. Under general anesthesia, the conjunctiva is cut away from the limbus with a circular incision and is separated from the sclera. The rectus muscles are taken on the thread of the holder. Using a trepan (diameter 5 mm), the cornea is perforated and removed. The prepared keratoprosthesis is fitted by passing the rear section of the optical element through the hole in the cornea until the supporting plate rests on its surface. The supporting plate of the keratoprosthesis is inserted in the previously prepared circular pocket in the corneal stroma and is fixed with interrupted sutures. The operation is completed by applying interrupted sutures on the conjunctiva.

The prosthesis is an optical element, fixed in a hole in a supporting base, which is made from an autograft, the patient's own nail plate, which does not lead to breakdown of the corneal tissue, rejection of the keratoprosthesis and formation of a retroprosthetic membrane. The supporting base has thickness decreasing in the radial direction from the center to the periphery, owing to which there is strong fixation of the supporting base of the keratoprosthesis and greater competence of treatment.

Example 6

Drainage for prophylaxis of scarring of the filtration zone in surgical correction of ophthalmic hypertension in the treatment of glaucoma. This is intended to provide directed and controlled outflow of intraocular fluid (IOF) from the anterior chamber of the eye via the intrascleral space.

The operation is performed in any of the free sectors of the globe between the rectus muscles. A single rectangular flap 10-12 mm long and 6 mm wide is formed, and is turned back onto the cornea. Near the limbus, after preliminary determination of the projection of Schlemm's canal, deep layers of the filtering zone are excised together with the sinus and trabecular meshwork in the form of a triangle with the dimensions 2.0×2.0×2.0 mm. Basal iridectomy is performed through the triangular hole obtained. A nail plate autograft of rectangular shape with dimensions of 5×6 mm is laid on the bottom of the scleral bed, completely covering the region of sinus trabeculectomy. The scleral flap was placed on top of the autograft, and then the flap was fixed at its apex with one U-shaped suture and with interrupted sutures along the sides on both sides, gripping the nail plate autograft in a single step. The operation led to a significant decrease in intraocular pressure, which in subsequent periods of observation gradually increased within the range of normal variation (16-22 mmHg); a year after the operation it was on average 19.6±1.6 mmHg, and it then stabilized at a level of about 20 mmHg (p>0.18). In the early postoperative period there was a smooth increase in the coefficient of the ease of outflow of aqueous, and by three months it had reached normal values (on average 0.21 mm/min/mmHg), which was evidence of the presence of controllable filtration of chamber aqueous into the intrascleral space, as well as functioning of the filtration zone for remote periods.

This indicated formation of an active drainage zone in the intrascleral space and active outflow of chamber aqueous from the anterior chamber. Examination of visual acuity showed that the operation leads to an increase in visual acuity, and its level remains stable in all periods of observation.

Investigation at various times after surgery for glaucoma using a nail plate autograft showed gradual disappearance of signs of edema of the eye membranes and improvement in condition of the optic nerve. Restoration of the drainage function of the eye led to restoration of the structure of the eye membranes.

For specialists in the field of ophthalmic surgery it will be obvious that various modifications and changes may be made to the present invention without departing from the essence or scope of the claims, which have not been reflected in the foregoing embodiment examples of the invention.

The invention claimed is:

1. A method for performing an ophthalmosurgical operation, comprising:
    producing a recipient bed in an ophthalmological area of a patient; and
    implanting an autograft in the recipient bed in the ophthalmological area of the patient,
    wherein a material used for making the autograft is a fragment of the patient's own nail plate,
    wherein the autograft is formed as a solid form with a structure and geometric characteristics adaptable to a shape of the recipient bed, and
    wherein after sterilization and prior to implantation, the autograft obtained is held in a dry atmosphere.

2. The method of claim 1, in which the ophthalmosurgical operation includes refractive intrastromal keratoplasty.

3. The method of claim 1, wherein the autograft has a shape of one or more segments.

4. The method of claim 1, wherein the fragment of the nail plate is obtained from a grown nail.

5. The method of claim 1, wherein the fragment of the nail plate is obtained from the patient's nail under local anaesthesia.

6. The method of claim 1, wherein the autograft is made in a form of a half-ring with an arc of 150°-170°, a height from 50 μm to 300 μm, and inside and outside diameters of 4 mm and 5 mm, respectively.

7. The method of claim 1, wherein the autograft is made in a form of a ring with an inside diameter from 0.5 mm to 7 mm, an outside diameter from 1.0 mm to 16 mm, and a height from 50 μm to 300 μm.

8. The method of claim 1, wherein the autograft is made in a form of a positive lens with a diameter from 1 mm to 7 mm, and with a central hole with a diameter from 0.1 mm to 5 mm.

9. The method of claim 1, wherein the autograft is made in the form of a plate from 1 mm to 25 mm long, from 1 mm to 20 mm wide, and with a thickness of 10 μm.

10. The method of claim 1, characterized in that the shape of the autograft is adapted mechanically using a diamond cutter monitored with an operating microscope or using laser processing.

11. A method of implanting an autograft, comprising:
    implanting an autograft into a recipient bed in an ophthalmological area of a patient,
    wherein the autograft is formed from a fragment of the patient's own nail plate, the autograft is a solid form having a structure and geometric characteristics adaptable to a shape of the recipient bed.

12. The method of claim 11, wherein the autograft is exposed to the recipient bed for a time period to adapt the autograft to the shape of the recipient bed as a result of natural swelling of the autograft due to moisture in the recipient bed.

13. The method of claim 11, comprising: (i) producing the recipient bed in the ophthalmological area of the patient prior to the step of implanting the autograft; and/or (ii) chemically treating the autograft prior to the step of implanting the autograft.

14. An ophthalmosurgical implant for a patient, comprising:
  an autograft comprising a fragment of the patient's own nail plate tissue,
  wherein the autograft is formed as a solid form with a structure and geometric characteristics adaptable to a shape of a recipient bed in an ophthalmological area of the patient for implantation in the recipient bed, and
  wherein after sterilization and prior to implantation, the autograft is held in a dry atmosphere.

15. The implant of claim 14, wherein the autograft is dimensioned to increase in size to adapt to the recipient bed upon implantation as a result of natural swelling of the autograft due to moisture in the recipient bed.

16. The implant of claim 15, wherein the autograft is configured to increase in volume to fill a tunnel of a corneal stroma of the patient upon transplantation.

17. The implant of claim 14, wherein the autograft is in a form of a half-ring with an arc of from 150° to 170°, a height from 50 μm to 300 μm, and inside and outside diameters of 4 mm and 5 mm, respectively.

18. The implant of claim 14, wherein the autograft is in a form of a ring with an inside diameter from 0.5 mm to 7 mm, an outside diameter from 1.0 mm to 16 mm, and a height from 50 μm to 300 μm.

19. The implant of claim 14, wherein the autograft is in a form of a positive lens.

20. The implant of claim 14, wherein the autograft is in a form of a plate from 1 mm to 25 mm long, from 1 mm to 20 mm wide, and with a thickness of 10 μm.

* * * * *